United States Patent
Bales

(10) Patent No.: US 12,336,741 B2
(45) Date of Patent: Jun. 24, 2025

(54) SURGICAL SYSTEM AND METHODS OF USE

(71) Applicant: WARSAW ORTHOPEDIC INC., Warsaw, IN (US)

(72) Inventor: Joel Bales, Hernando, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 202 days.

(21) Appl. No.: 18/121,396

(22) Filed: Mar. 14, 2023

(65) Prior Publication Data

US 2024/0307095 A1 Sep. 19, 2024

(51) Int. Cl.
*A61B 17/70* (2006.01)

(52) U.S. Cl.
CPC .................. *A61B 17/705* (2013.01)

(58) Field of Classification Search
CPC .............. A61B 17/705; A61B 17/7055; A61B 17/6458; A61B 17/6466; A61B 17/7043; A61B 17/7049; A61B 17/7052
See application file for complete search history.

(56) References Cited

U.S. PATENT DOCUMENTS

| | | | | | |
|---|---|---|---|---|---|
| 5,133,717 | A * | 7/1992 | Chopin | .............. | A61B 17/7055 606/264 |
| 6,565,564 | B2 * | 5/2003 | Hoffman | ............ | A61B 17/6466 606/59 |
| 8,998,961 | B1 * | 4/2015 | Ziemek | ................ | A61B 17/705 606/260 |
| 9,463,050 | B2 * | 10/2016 | Schwend | ............. | A61B 17/705 |
| 2006/0079892 | A1 * | 4/2006 | Roychowdhury | . | A61B 17/7044 606/279 |
| 2007/0191844 | A1 * | 8/2007 | Carls | .................... | A61B 17/705 606/86 A |
| 2010/0280552 | A1 * | 11/2010 | Lee | ....................... | A61B 17/705 606/264 |
| 2015/0173804 | A1 * | 6/2015 | Gepstein | ............ | A61B 17/7002 606/279 |
| 2016/0183981 | A1 * | 6/2016 | Schlaepfer | ......... | A61B 17/7056 606/324 |
| 2023/0200860 | A1 * | 6/2023 | Ichelmann | ......... | A61B 17/7052 606/270 |

* cited by examiner

*Primary Examiner* — Lynnsy M Summitt
(74) *Attorney, Agent, or Firm* — Sorell, Lenna & Schmidt, LLP

(57) ABSTRACT

A spine rod connector includes a first portion having end surfaces and side surfaces. The first portion includes top and bottom surfaces. The first portion includes a first aperture extending between and through the end surfaces and spaced apart holes extending through the top surface such that the holes are in communication with the first aperture. The spine rod connector includes a second portion having end surfaces and side surfaces. The second portion includes top and bottom surfaces. The second portion includes a second aperture extending between and through the side surfaces of the second portion and spaced apart holes extending through the top surface of the second portion such that the holes of the second portion are in communication with the second aperture.

20 Claims, 9 Drawing Sheets

SURGICAL SYSTEM AND METHODS OF USE

TECHNICAL FIELD

The present disclosure generally relates to medical devices for the treatment of musculoskeletal disorders, and more particularly to a surgical system and method for correction of a spine disorder.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. Correction treatments used for positioning and alignment may employ implants, such as vertebral rods and bone screws for stabilization of a treated section of a spine. This disclosure describes an improvement over these prior technologies.

SUMMARY

In one embodiment, in accordance with the principles of the present disclosure, a surgical system comprises a spine rod connector having a first portion and a second portion. The first portion comprises opposite first and second end surfaces and opposite first and second side surfaces each extending from the first end surface to the second end surface. The first portion comprises opposite top and bottom surfaces. The end and side surfaces each extend from the top surface to the bottom surface. The first portion comprises a first aperture extending between and through the end surfaces and spaced apart holes extending through the top surface such that the holes are in communication with the first aperture. The second portion comprises opposite first and second end surfaces and opposite first and second side surfaces each extending from the first end surface of the second portion to the second end surface of the second portion. The second portion comprises opposite top and bottom surfaces, The end and side surfaces of the second portion each extend from the top surface of the second portion to the bottom surface of the second portion. The second portion comprises a second aperture extending between and through the side surfaces of the second portion and spaced apart holes extending through the top surface of the second portion such that the holes of the second portion are in communication with the second aperture.

In some embodiments, the first aperture defines a first longitudinal axis disposed in a first plane and the second aperture defines a second longitudinal axis disposed in a second plane that is proximal to the first plane. In some embodiments, the top surface of the second portion is planar from the first end surface of the second portion to the second end surface of the second portion. In some embodiments, the top surface of the second portion is positioned between the top surface of the first portion and the bottom surface of the first portion. In some embodiments, the bottom surface of the second portion is positioned between the top surface of the first portion and the bottom surface of the first portion. In some embodiments, the second portion comprises a cutout extending through the first end surface of the second portion and the top surface of the second portion, the cutout being aligned with one of the holes of the first portion. In some embodiments, the second portion comprises a cutout extending through the second end surface of the second portion and the top surface of the second portion, the cutout being aligned with one of the holes of the first portion. In some embodiments, the second portion comprises a first cutout extending through the first end surface of the second portion and the top surface of the second portion, the first cutout being aligned with one of the holes of the first portion; and the second portion comprises a second cutout extending through the second end surface of the second portion and the top surface of the second portion, the second cutout being aligned with another one of the holes of the first portion. In some embodiments, the first portion includes only the first aperture extending through the end surfaces of the first portion and the second portion includes only the second aperture extending through the side surfaces of the second portion. In some embodiments, the holes of the second portion are positioned between the holes of the first portion. In some embodiments, the first aperture extends perpendicular to the second aperture. In some embodiments, the first aperture is in communication with the second aperture. In some embodiments, the holes are each threaded for engagement with a threaded setscrew. In some embodiments, the second portion is monolithically formed with the first portion. In some embodiments, the first aperture is positioned between the holes of the second portion.

In some embodiments, a surgical system comprises the spine rod connector, a first spinal rod positioned in the first aperture and a second spinal rod positioned in the second aperture. In some embodiments, the first aperture and the first spinal rod each have a non-circular diameter to prevent rotation of the first spinal rod within the first aperture and the second aperture and the second spinal rod each have a non-circular diameter to prevent rotation of the second spinal rod within the second aperture. some embodiments, the surgical system further comprises setscrews disposed in the holes of the first portion to fix the first spinal rod relative to the spine rod connector; and setscrews disposed in the holes of the second portion to fix the second spinal rod relative to the spine rod connector.

In one embodiment, a spine rod connector comprises a first portion and a second portion. The first portion comprises opposite first and second end surfaces and opposite first and second side surfaces each extending from the first end surface to the second end surface. The first portion comprises opposite top and bottom surfaces. The end and side surfaces each extend from the top surface to the bottom surface. The first portion comprises a first aperture extending between and through the end surfaces and spaced apart holes extending through the top surface such that the holes are in communication with the first aperture. The second portion comprises opposite first and second end surfaces and opposite first and second side surfaces each extending from the first end surface of the second portion to the second end surface of the second portion. The second portion comprises opposite top and bottom surfaces. The end and side surfaces of the second portion each extend from the top surface of the second portion to the bottom surface of the second portion. The second portion comprises a second aperture extending between and through the side surfaces of the second portion and spaced apart holes extending through the top surface of the second portion such that the holes of the second portion are in communication with the second aperture. The first aperture defines a first longitudinal axis disposed in a first plane and the second aperture defines a second longitudinal axis disposed in a second plane that is proximal to the first plane. The top surface of the second portion is positioned between the top surface of the first portion and the bottom surface of the first portion. The bottom surface of the second portion is positioned between the top surface of the first portion and the bottom surface of the first portion. The second portion comprises a first cutout extending through the first end surface of the second portion and the top surface of the second portion, the first cutout being aligned with one of the holes of the first portion. The second portion comprises a second cutout extending through the second end surface of the second portion and the top surface of the second portion, the second cutout being aligned with another one of the holes of the first portion. The first portion includes only the first aperture extending through the end surfaces of the first portion and the second portion includes only the second aperture extending through the side surfaces of the second portion. The first aperture extends perpendicular to the second aperture. The first aperture is in communication with the second aperture. The second portion is monolithically formed with the first portion. The first aperture is positioned between the holes of the second portion.

In one embodiment, in accordance with the principles of the present disclosure, a surgical system comprises a spine rod connector comprising a first portion and a second portion. The first portion comprises opposite first and second end surfaces and opposite first and second side surfaces each extending from the first end surface to the second end surface. The first portion comprises opposite top and bottom surfaces. The end and side surfaces each extend from the top surface to the bottom surface. The first portion comprises a first aperture extending between and through the end surfaces and spaced apart holes extending through the top surface such that the holes are in communication with the first aperture. The second portion comprises opposite first and second end surfaces and opposite first and second side surfaces each extending from the first end surface of the second portion to the second end surface of the second portion. The second portion comprises opposite top and bottom surfaces. The end and side surfaces of the second portion each extend from the top surface of the second portion to the bottom surface of the second portion. The second portion comprises a second aperture extending between and through the side surfaces of the second portion and spaced apart holes extending through the top surface of the second portion such that the holes of the second portion are in communication with the second aperture. The system includes a first spinal rod positioned in the first aperture. The system includes a second spinal rod positioned in the second aperture. The system includes setscrews disposed in the holes of the first portion to fix the first spinal rod relative to the spine rod connector. The system includes setscrews disposed in the holes of the second portion to fix the second spinal rod relative to the spine rod connector. The first aperture and the first spinal rod each have a non-circular diameter to prevent rotation of the first spinal rod within the first aperture and the second aperture and the second spinal rod each have a non-circular diameter to prevent rotation of the second spinal rod within the second aperture. The first aperture defines a first longitudinal axis disposed in a first plane and the second aperture defines a second longitudinal axis disposed in a second plane that is proximal to the first plane. The top surface of the second portion is positioned between the top surface of the first portion and the bottom surface of the first portion. The bottom surface of the second portion is positioned between the top surface of the first portion and the bottom surface of the first portion. The second portion comprises a first cutout extending through the first end surface of the second portion and the top surface of the second portion, the first cutout being aligned with one of the holes of the first portion. The second portion comprises a second cutout extending through the second end surface of the second portion and the top surface of the second portion, the second cutout being aligned with another one of the holes of the first portion. The first portion includes only the first aperture extending through the end surfaces of the first portion and the second portion includes only the second aperture extending through the side surfaces of the second portion. The first aperture extends perpendicular to the second aperture. The first aperture is in communication with the second aperture. The second portion is monolithically formed with the first portion. The first aperture is positioned between the holes of the second portion.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

Figure 1:
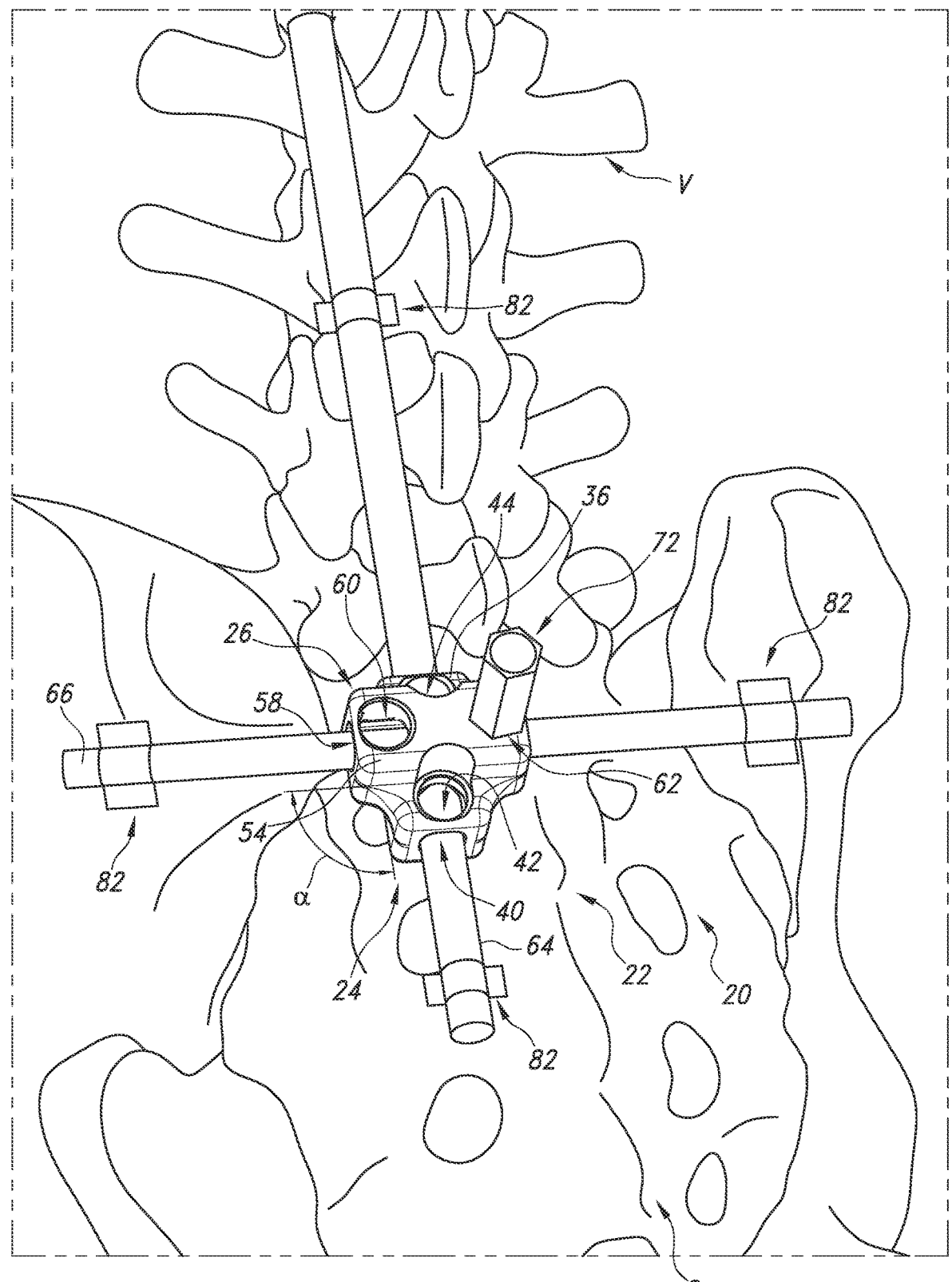
FIG. 1 is a plan view of a spinal implant of a surgical system disposed with vertebrae, rods of the surgical system and a setscrew of the surgical system, in accordance with the principles of the present disclosure.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including implants, related components and methods of employing the surgical system in accordance with the principles of the present disclosure. Alternate embodiments are also disclosed. Reference is made in detail to the exemplary embodiments of a surgical system 20, which are illustrated in the accompanying figures.

The components of surgical system 20 can be fabricated from biologically acceptable materials suitable for medical applications, including metals, synthetic polymers, ceramics and bone material and/or their composites. For example, the components of surgical system 20, individually or collectively, can be fabricated from materials such as stainless steel alloys, aluminum, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of surgical system 20 may have material composites, including the above materials, to achieve various desired characteristics such as strength, rigidity, elasticity, compliance, biomechanical performance, durability and radiolucency or imaging preference. The components of surgical system 20, individually or collectively, may also be fabricated from a heterogeneous material such as a combination of two or more of the above-described materials. The components of surgical system 20 may be monolithically formed, integrally connected or include fastening elements and/or instruments, as described herein.

Surgical system 20 is employed, for example, with a fully open surgical procedure, a minimally invasive procedure including percutaneous techniques, and mini-open surgical techniques to deliver and introduce instrumentation and/or one or more spinal implants, such as, for example, one or more components of a bone fastener, at a surgical site of a patient, which includes, for example, a spine. In some embodiments, the spinal implant can include one or more components of one or more spinal constructs, such as, for example, interbody devices, interbody cages, bone fasteners, spinal rods, tethers, connectors, plates and/or bone graft, and can be employed with various surgical procedures including surgical treatment of a cervical, thoracic, lumbar and/or sacral region of a spine.

The surgical system disclose herein includes a spine rod connector. In some embodiments, the spine rod connector is configured for use in, among other things, sacrectomy surgery. In particular, during sacrectomy surgery, rods are attached to the iliac and lumbar spine. These rods can cross such that the rods extend at 90 degrees relative to one another. The rods may be posterior or anterior. The spine rod connector disclosed herein is configured easily facilitate the two crossing rods. For example, the spine rod connector is configured to address crossing rods in a compact versatile way so that the number of crossing rods or the location and orientation of the rods can be addressed easily. The ease of use and versatility of the spine rod connector offers surgeons a fast and robust solution to a complex surgery. In some embodiments, the spine rod connector includes rod apertures that are spaced apart in different planes and overlapping.

The surgical system disclose herein includes the spine rod connector and other components for use with the spine rod connector, such as, for example, a plurality of spinal rods and a plurality of setscrews, as discussed herein. Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Surgical system 20 includes an implant, such as, for example, a spine rod connector 22. Connector 22 includes a first portion 24 and a second portion 26. In some embodiments, portion 24 and portion 26 are integrally and/or monolithically formed such that portion 26 cannot be removed from portion 24 without breaking portion 26 and/or portion 24, and vice versa. In some embodiments, at least one of portion 24 and portion 26 is made from at least one of the materials discussed herein. For example, in some embodiments, portion 24 and/or portion 26 is/are made from a material that allows portion 24 and/or portion 26 to flex and/or bend without breaking portion 24 and/or portion 26 when stresses are applied to portion 24 and/or portion 26 by one or more spinal rods. In some embodiments, portion 24 and/or portion 26 is/are made from a rigid material that causes portion 24 and/or portion 26 to break when stresses are applied to portion 24 and/or portion 26 by one or more spinal rods.

Portion 24 comprises a first end surface 28 and an opposite end surface 30. Portion 24 comprises a first side surface 32 and an opposite second side surface 34 each extending from surface 28 to surface 30. Portion 24 comprises a top surface 36 and an opposite bottom surface 38. In some embodiments, surface 38 extends parallel to surface 36. Surfaces 30, 32, 34, 36 each extend from surface 36 to surface 38. Portion 24 comprises a first aperture 40 extending between and through surfaces 28, 30 and spaced apart first and second holes 42, 44 each extending through surface 36 such that holes 42, 44 are each in communication with aperture 40.

In some embodiments, portion 24 includes only aperture 40 extending through surfaces 28, 30. That is, portion 24 does not include any aperture, channel, passageway, conduit, etc. that extends through surfaces 28, 30 in addition to aperture 40. In some embodiments, aperture 40 is disposed equidistant between surfaces 32, 34 and/or equidistant between surfaces 36, 38. That is, a midpoint of a diameter of aperture 40 is disposed equidistant between surfaces 32, 34 and/or equidistant between surfaces 36, 38. In some embodiments, aperture 40 may have various cross section configurations, such as, for example, circular, oval, oblong, triangular, rectangular, square, polygonal, irregular, uniform, non-uniform, variable, tubular and/or tapered. In some embodiments, aperture 40 has a uniform diameter along an entire length of aperture 40. That is, aperture 40 has a uniform diameter from surface 28 to surface 30. In some embodiments, holes 42, 44 are each threaded for engagement with a coupling member, such as, for example, a setscrew such that the setscrews directly engage a spinal construct, such as, for example, a spinal rod positioned within aperture 40 to prevent movement of the spinal rod relative to connector 22, as discussed herein. In some embodiments, surface 28 is entirely planar. That is, surface 28 is planar from surface 32 to surface 34 and/or from surface 36 to surface 38. In some embodiments, surface 30 is entirely planar. That is, surface 30 is planar from surface 32 to surface 34 and/or from surface 36 to surface 38. In some embodiments, surface 38 is entirely planar. That is, surface 38 is planar from surface 32 to surface 34 and/or from surface 28 to surface 30. In some embodiments, holes 42, 44 extend parallel to one another. In some embodiments, hole 42 and/or hole 44 extends perpendicular to aperture 40. In some embodiments, hole 42 may be disposed at alternative orientations relative to hole 44 and/or at least one of holes 42, 44 may be disposed at alternate orientations, relative to aperture 40, such as, for example, transverse and/or other angular orientations such as acute or obtuse, co-axial and/or may be offset or staggered.

Portion 26 is coupled to portion 24 and comprises a first end surface 46 and an opposite end surface 48. Portion 26 comprises a first side surface 50 and an opposite second side surface 52 each extending from surface 46 to surface 48. Portion 26 comprises a top surface 54 and an opposite bottom surface 56. In some embodiments, surface 56 extends parallel to surface 54. In some embodiments, surface 54 and/or surface 56 extends parallel to surface 36 and/or surface 38. Surfaces 46, 48, 50, 52 each extend from surface 54 to surface 56. Portion 26 comprises a second aperture 58 extending between and through surfaces 50, 52 and spaced apart first and second holes 60, 62 each extending through surface 54 such that holes 60, 62 are each in communication with aperture 58.

In some embodiments, channel 58 is positioned equidistant between surface 28 and surface 30 and/or channel 40 is positioned equidistant between surface 50 and surface 52. In some embodiments, portion 26 includes only aperture 58 extending through surfaces 50, 52. That is, portion 26 does not include any aperture, channel, passageway, conduit, etc. that extends through surfaces 50, 52 in addition to aperture 58. In some embodiments, aperture 58 is disposed equidistant between surfaces 48, 50 and/or equidistant between surfaces 54, 56. That is, a midpoint of a diameter of aperture 58 is disposed equidistant between surfaces 48, 50 and/or equidistant between surfaces 54, 56. In some embodiments, aperture 58 may have various cross section configurations, such as, for example, circular, oval, oblong, triangular, rectangular, square, polygonal, irregular, uniform, non-uniform, variable, tubular and/or tapered. In some embodiments, aperture 58 has a uniform diameter along an entire length of aperture 58. That is, aperture 58 has a uniform diameter from surface 50 to surface 52. In some embodiments, holes 60, 62 are each threaded for engagement with a coupling member, such as, for example, a setscrew such that the setscrews directly engage a spinal construct, such as, for example, a spinal rod positioned within aperture 58 to prevent movement of the spinal rod relative to connector 22, as discussed herein. In some embodiments, holes 60, 62 are positioned between hole 42 and hole 44. In some embodiments, surface 50 is entirely planar. That is, surface 50 is planar from surface 46 to surface 48 and/or from surface 54 to surface 56. In some embodiments, surface 52 is entirely planar. That is, surface 52 is planar from surface 46 to surface 48 and/or from surface 54 to surface 56. In some embodiments, holes 60, 62 extend parallel to one another. In some embodiments, hole 60 and/or hole 62 extends perpendicular to aperture 58. In some embodiments, hole 60 may be disposed at alternative orientations relative to hole 62 and/or at least one of holes 60, 62 may be disposed at alternate orientations, relative to aperture 58, such as, for example, transverse and/or other angular orientations such as acute or obtuse, co-axial and/or may be offset or staggered.

In some embodiments, at least a portion of surface 54 is planar from surface 50 to surface 52. That is, a portion of surface 54 between holes 60, 62 and surface 46 is planar from surface 50 to surface 52 and a portion of surface 54 between holes 60, 62 and surface 48 is planar from surface 50 to surface 52. As such, a portion of surface 54 that hole 60 extends through is co-planar and/or level with a portion of surface 54 that hole 62 extends through. In some embodiments, at least a portion of surface 54 is planar from surface 46 to surface 48. That is, at least a portion of surface 54 is planar from surface 50 to surface 52 and at least a portion of surface 54 is planar from surface 46 to surface 48. In some embodiments, at least one of the portions of surface 54 that is planar from surface 50 to surface 52 intersects at least one of the portions of surface 54 that is planar from surface 46 to surface 48.

Aperture 40 defines a longitudinal axis X1 and aperture 58 defines a longitudinal axis X2. In some embodiments, axis X1 is a central longitudinal axis and axis X2 is a central longitudinal axis. In some embodiments, aperture 40 is entirely linear such that aperture 40 extends parallel to axis X1 along an entire length of aperture 40. In some embodiments, aperture 58 is entirely linear such that aperture 58 extends parallel to axis X2 along an entire length of aperture 58. In some embodiments, surfaces 32, 34 extend parallel to one another and surfaces 46, 48 extend parallel to one another such that surfaces 32, 34 are disposed at an angle α relative to surfaces 46, 48. Aperture 58 is thus disposed at angle α relative to aperture 40 such that axis X2 is disposed at angle α relative to axis X1. In some embodiments, angle α is between 0 and 180 degrees. In some embodiments, angle α is between 10 and 170 degrees. In some embodiments, angle α is between 20 and 160 degrees. In some embodiments, angle α is between 30 and 160 degrees. In some embodiments, angle α is between 40 and 150 degrees. In some embodiments, angle α is between 50 and 140 degrees. In some embodiments, angle α is between 60 and 130 degrees. In some embodiments, angle α is between 70 and 120 degrees. In some embodiments, angle α is between 80 and 110 degrees. In some embodiments, angle α is between 90 and 100 degrees. In some embodiments, angle α is 90 degrees. In some embodiments, disposing apertures 40, 58 at angle α disposes a spinal rod, such as, for example, a first spinal rod 64 disposed in aperture 40 is disposed at angle α relative to a spinal rod, such as, for example, a second spinal rod 66 that is disposed in aperture 58.

Figure 2:
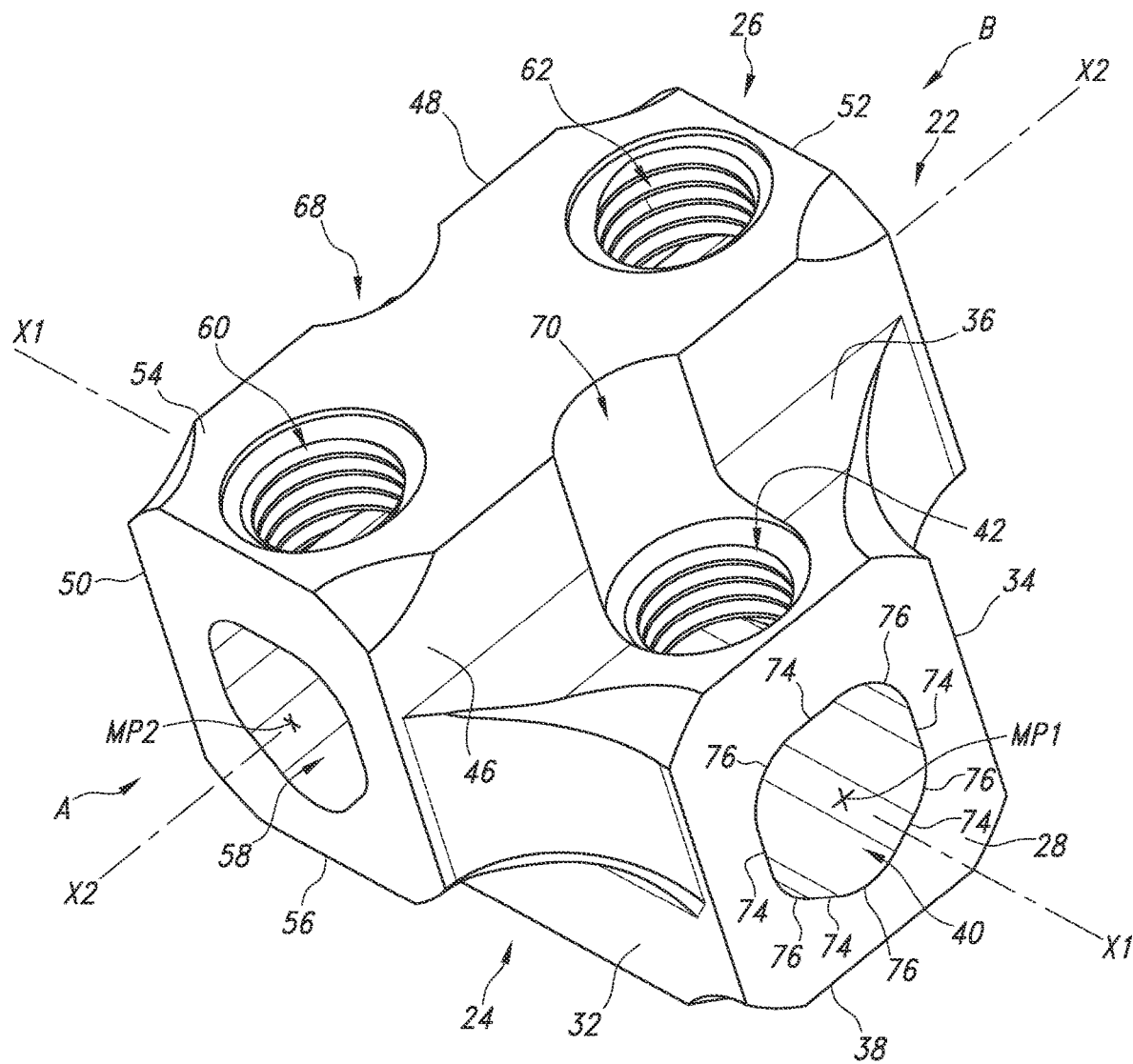
FIG. 2 is a perspective view of the spinal implant shown in FIG. 1.
Figure 3:
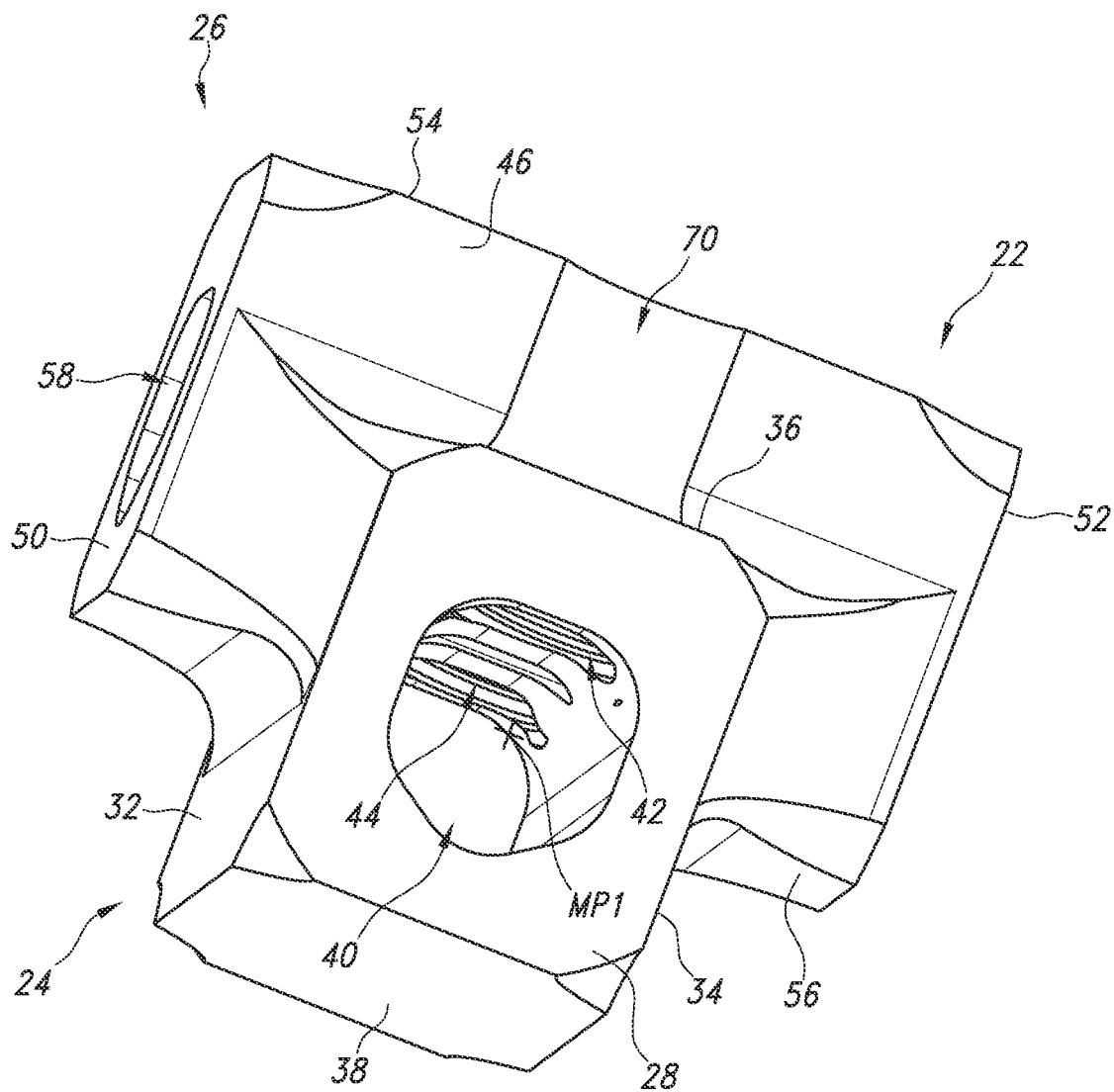
FIG. 3 is a perspective, cross-sectional view of the spinal implant shown in FIG. 1.
Figure 4:
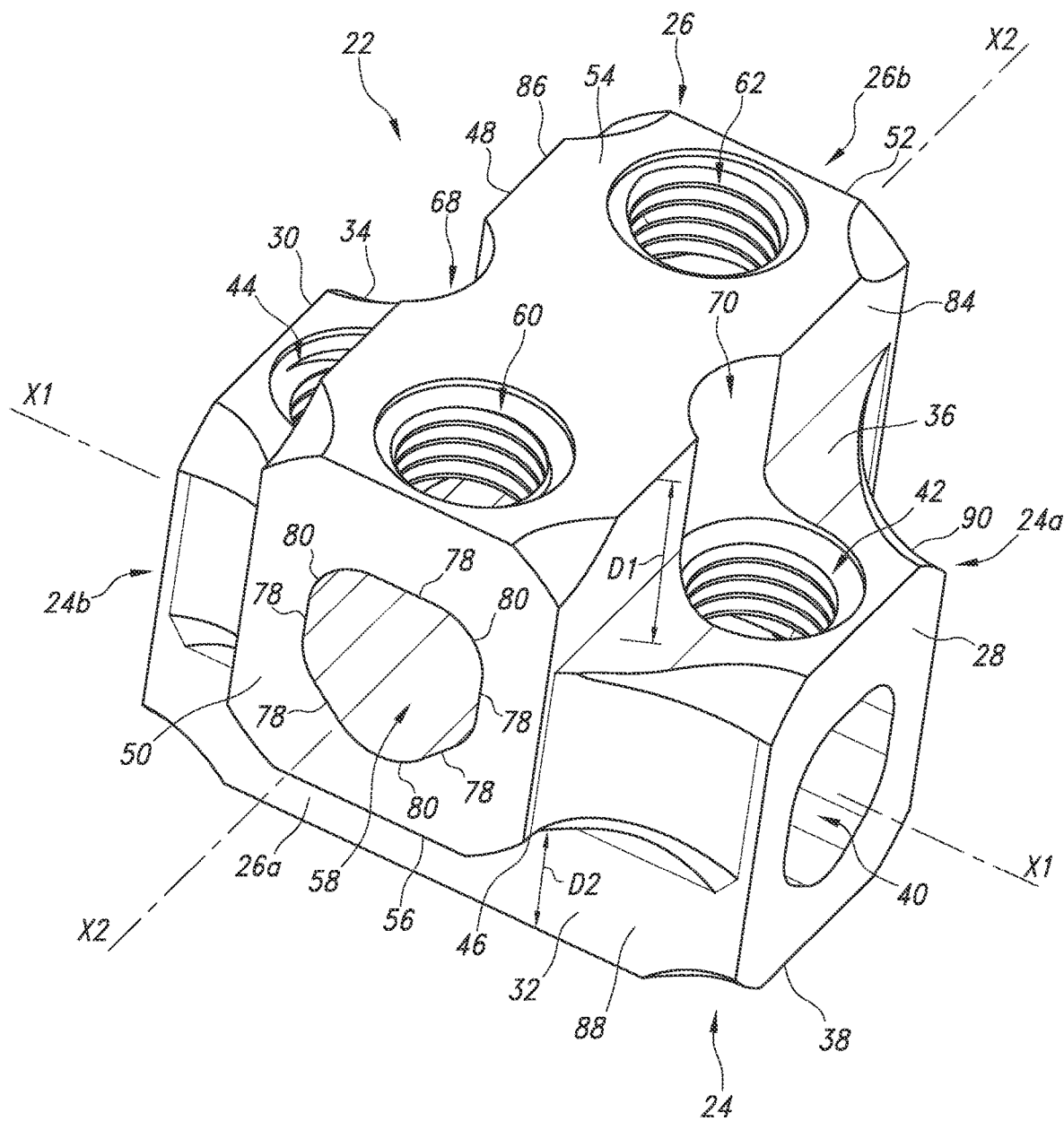
FIG. 4 is a perspective view of the spinal implant shown in FIG. 1.

In some embodiments, aperture 40 and rod 64 each have a non-circular diameter, are textured or have a non-circular diameter and are textured to prevent rotation of rod 64 when rod 64 is positioned within aperture 40 and/or aperture 58 and rod 66 each have a non-circular diameter or are textured to prevent rotation of rod 66 when rod 66 is positioned within aperture 58. That is, aperture 40 has a cross-sectional configuration that corresponds or matches that of rod 64 to prevent rotation of rod 64 within aperture 40 and/or aperture 58 has a cross-sectional configuration that corresponds or matches that of rod 66 to prevent rotation of rod 66 within aperture 58. For example, in some embodiments, portion 24 includes an inner surface having a plurality of planar sections 74 and a plurality of arcuate sections 76 that define aperture 40. As shown in FIG. 2, one of sections 76 is positioned between adjacent sections 74, and vice versa. Similarly, in some embodiments, portion 26 includes an inner surface having a plurality of planar sections 78 and a plurality of arcuate sections 80 that define aperture 58. As shown in FIG. 4, one of sections 80 is positioned between adjacent sections 78, and vice versa. In some embodiments, rod 64 has a configuration that includes a size, shape and diameter and rod 66 has the same configuration as rod 64. In such configurations, aperture 40 and aperture 58 each have a configuration that includes a size, shape and diameter and the configurations or rods 64, 66 match and/or correspond to the configurations of apertures 40, 58.

Figure 5:
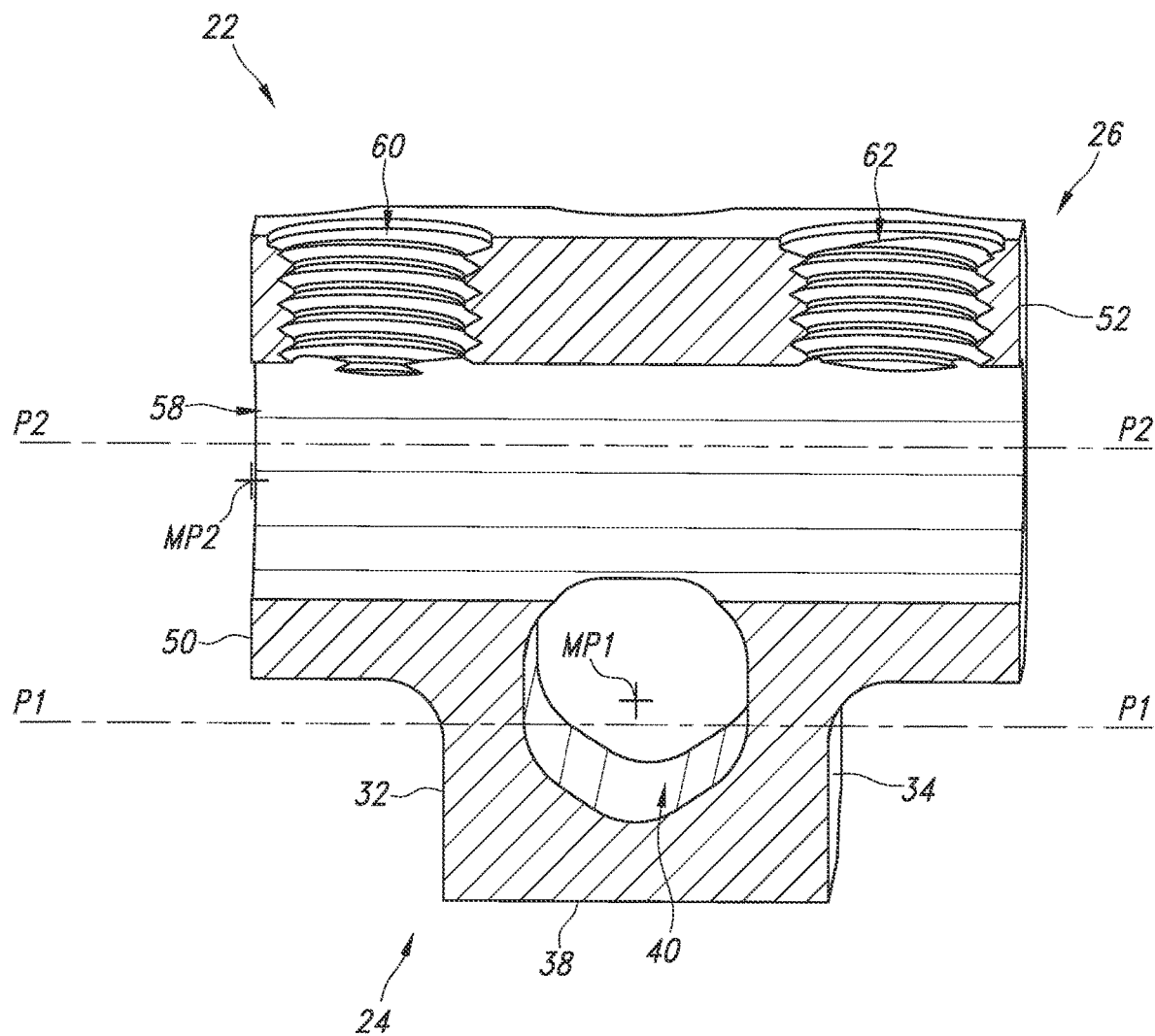
FIG. 5 is a side, cross-sectional view of the spinal implant shown in FIG. 1.
Figure 6:
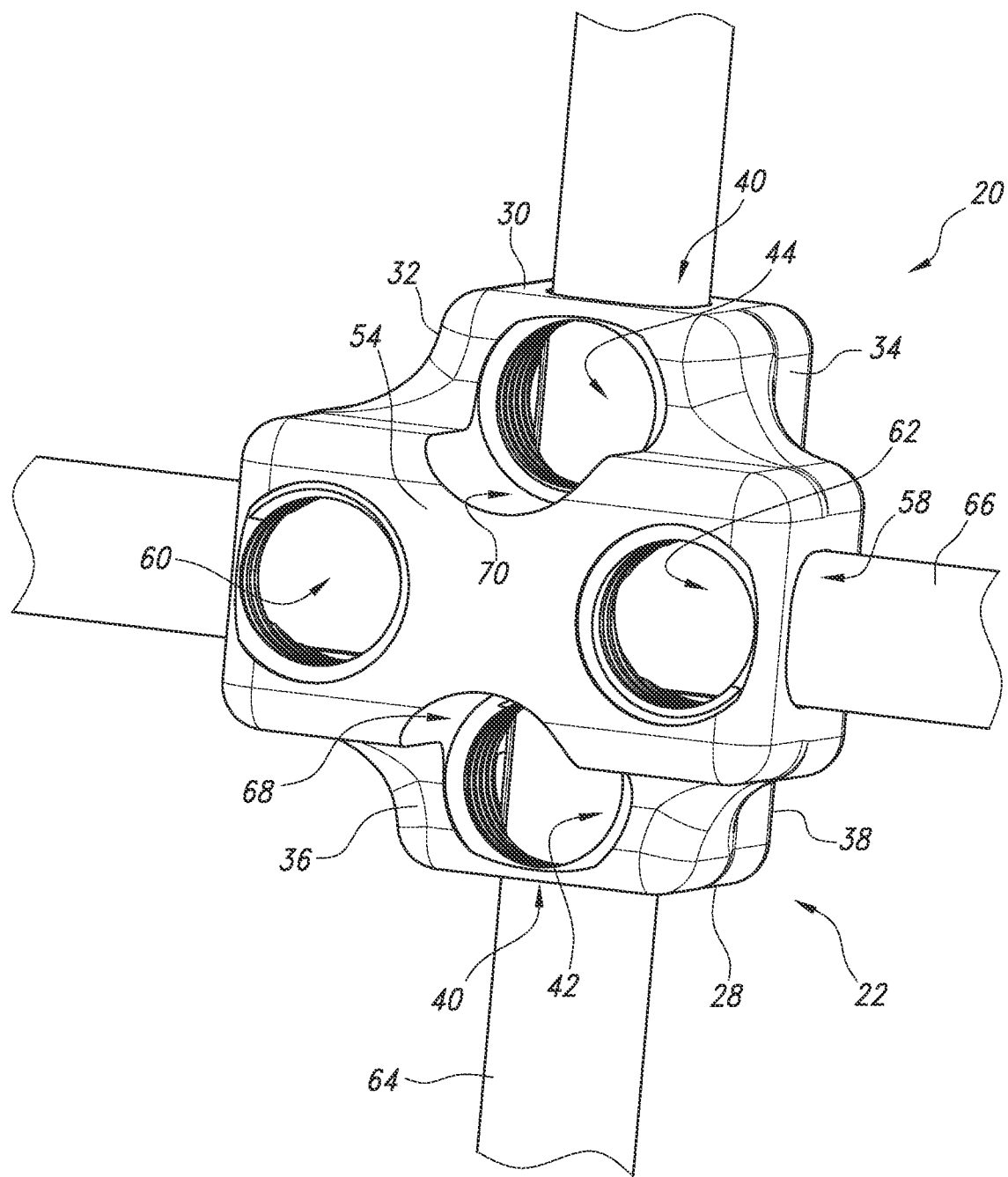
FIG. 6 is a plan view showing the rods shown in FIG. 1 disposed with the spinal implant shown in FIG. 1.

In some embodiments, at least a portion of aperture 40, such as, for example, MP1 is disposed in a first plane P1 and at least a portion of aperture 58, such as, for example, MP2 is disposed in a second plane P2 that extends parallel to plane P1. Plane P2 is disposed proximal to plane P2, as shown in FIG. 5, for example. This allows a spinal rod, such as, for example, rod 64 that is disposed in aperture 40 to be positioned distal to a spinal rod, such as, for example, rod 66 that is disposed in aperture 58. This allows a bottom or distal surface of rod 64 to be distal to a bottom or distal surface of rod 66 when rod 64 is disposed in aperture 40 and rod 66 is disposed in aperture 58. Similarly, this allows a top or proximal surface of rod 66 to be proximal to a top or proximal surface of rod when rod 64 is disposed in aperture 40 and rod 66 is disposed in aperture 58. In some embodiments, aperture 58 is in communication with aperture 40. In particular, in some embodiments, aperture 58 intersects and/or overlaps a portion of aperture 40, as shown in FIG. 5. This allows spinal rod 66 to directly engage spinal rod 64 when rod 64 is disposed in aperture 40 and rod 66 is disposed in aperture 58. In some embodiments, planes P1, P2 extend parallel to axis X1, axis X2, aperture 40 and/or aperture 58. In some embodiments, plane P1 is positioned equidistant between surfaces 36, 38 and/or extends parallel to surface 36 and/or surface 38. In some embodiments, plane P2 is positioned equidistant between surfaces 54, 56 and/or extends parallel to surface 54 and/or surface 56. In some embodiments, portion 26 is coupled to portion 24 such that surface 54 is positioned between surfaces 36, 38 and surface 56 is positioned between surfaces 36, 38. This offset configuration between portion 24 and portion 26 allows plane P2 to be positioned proximal to plane P1 and hence for aperture 58 to be positioned proximal to aperture 40. In some embodiments, surfaces 36, 54 extend parallel to one another and surface 54 is spaced a first distance D1 apart from surface 36; and surfaces 38, 56 extend parallel to one another and surface 56 is spaced a second distance D2 apart from surface 38, as shown in FIG. 4. In some embodiments, distance D2 is equal to distance D1. In some embodiments, distance D2 is more or less than distance D1.

In some embodiments, portion 26 comprises a first cutout 68 extending through surface 48 and surface 54 such that cutout 68 is aligned with hole 44 and a second cutout 70 extending through surface 46 and surface 54 such that cutout 70 is aligned with hole 42. In some embodiments, cutout 68 provides space and/or clearance for a coupling member, such as, for example, a setscrew 72 that is threaded with hole 44 such that setscrew 72 directly engages rod 64 when rod 64 is disposed in aperture 40 to fix rod 64 relative to connector 22. Similarly, cutout 70 provides space and/or clearance for a coupling member, such as, for example, setscrew 72 that is threaded with hole 42 such that setscrew 72 directly engages rod 64 when rod 64 is disposed in aperture 40 to fix rod 64 relative to connector 22. In some embodiments, cutouts 68, 70 are concavely curved and/or include a continuous radius of curvature to correspond and/or match the configuration of an outer surface of setscrew 72, for example. In some embodiments, cutouts 68, 70 are each positioned equidistant between surfaces 44, 46 and/or equidistant between surfaces 50, 52. In some embodiments, a surface that defines cutout 68 is continuous with a surface that defines hole 44 and/or a surface that defines cutout 70 is continuous with a surface that defines hole 42.

In some embodiments, connector 22 is configured such that part of a first section 24a of portion 24 extends from a first side 84 of portion 26 and part of a second section 24b of portion 24 extends from an opposite second side 86 of portion 26, as shown in FIG. 4, for example. That is, surfaces 32, 34, 36 of section 24a each extend from surface 46 of portion 26 and surfaces 32, 34, 36 of section 24b each extend from surface 48 of portion 26. Surface 36 of section 24a is spaced apart from surfaces 32, 34, 36 of section 24b by portion 26. That is, surface 36 of section 24a is spaced apart from surface 36 of section 24b by surfaces 46, 48 of portion 26. Surface 38, on the other hand, extends continuously from surface 28 to surface 30.

In some embodiments, connector 22 is configured such that part of a first section 26a of portion 26 extends from a first side 88 of portion 24 and part of a second section 26b of portion 26 extends from an opposite second side 90 of portion 24, as shown in FIG. 4, for example. That is, surfaces 46, 48, 56 of section 26a each extend from surface 32 of portion 24 and surfaces 46, 48, 56 of section 26b each extend from surface 34 of portion 24. Surface 56 of section 26a is spaced apart from surface 56 of section 26b by portion 24. That is, surface 56 of section 26a is spaced apart from surface 56 of section 26b by surfaces 32, 34 of portion 24. Surface 54, on the other hand, extends continuously from surface 50 to surface 52.

Figure 8:
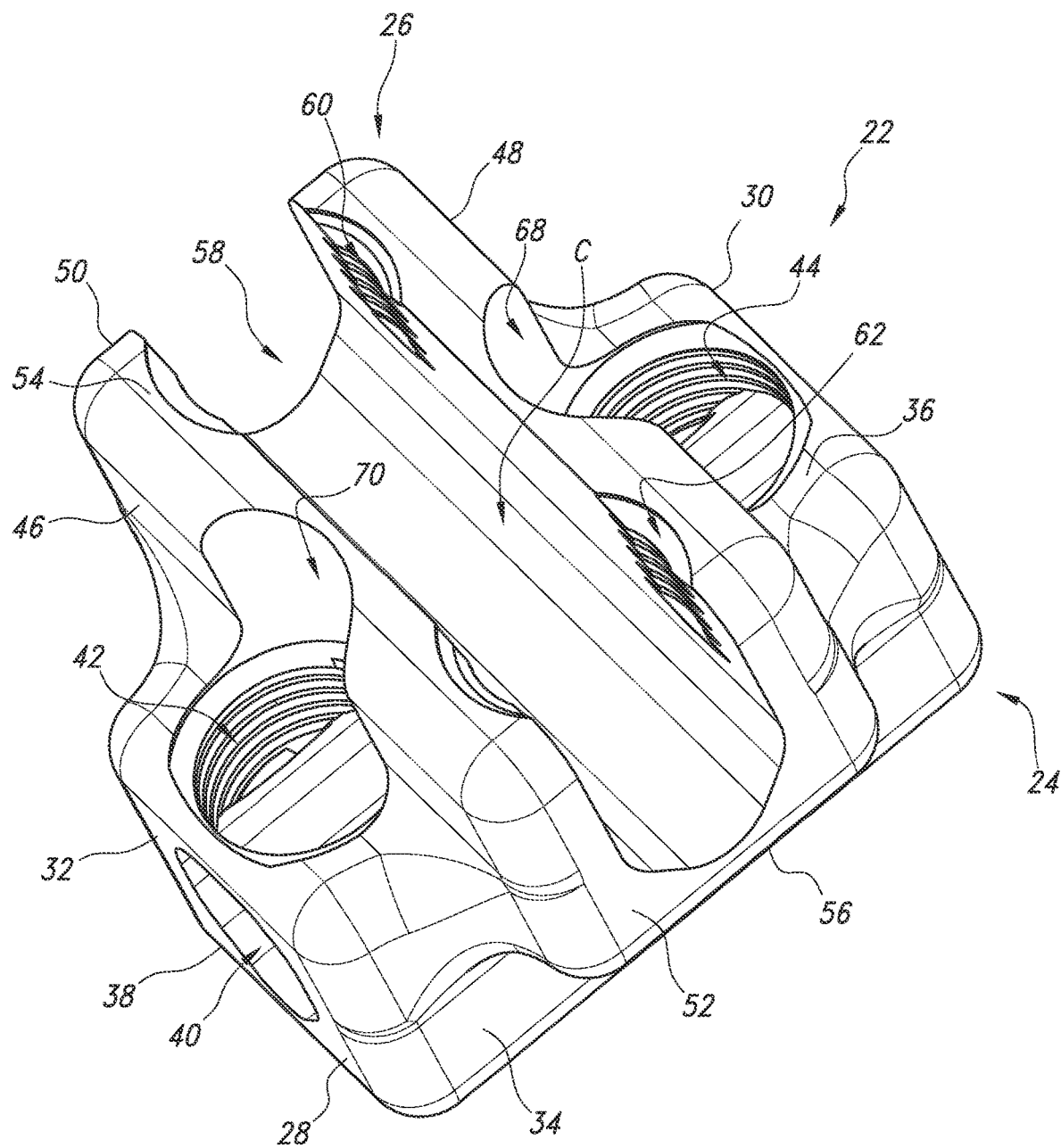
FIG. 8 is a perspective view of one embodiment of the spinal implant shown in FIG. 1, in accordance with the principles of the present disclosure.
Figure 9:
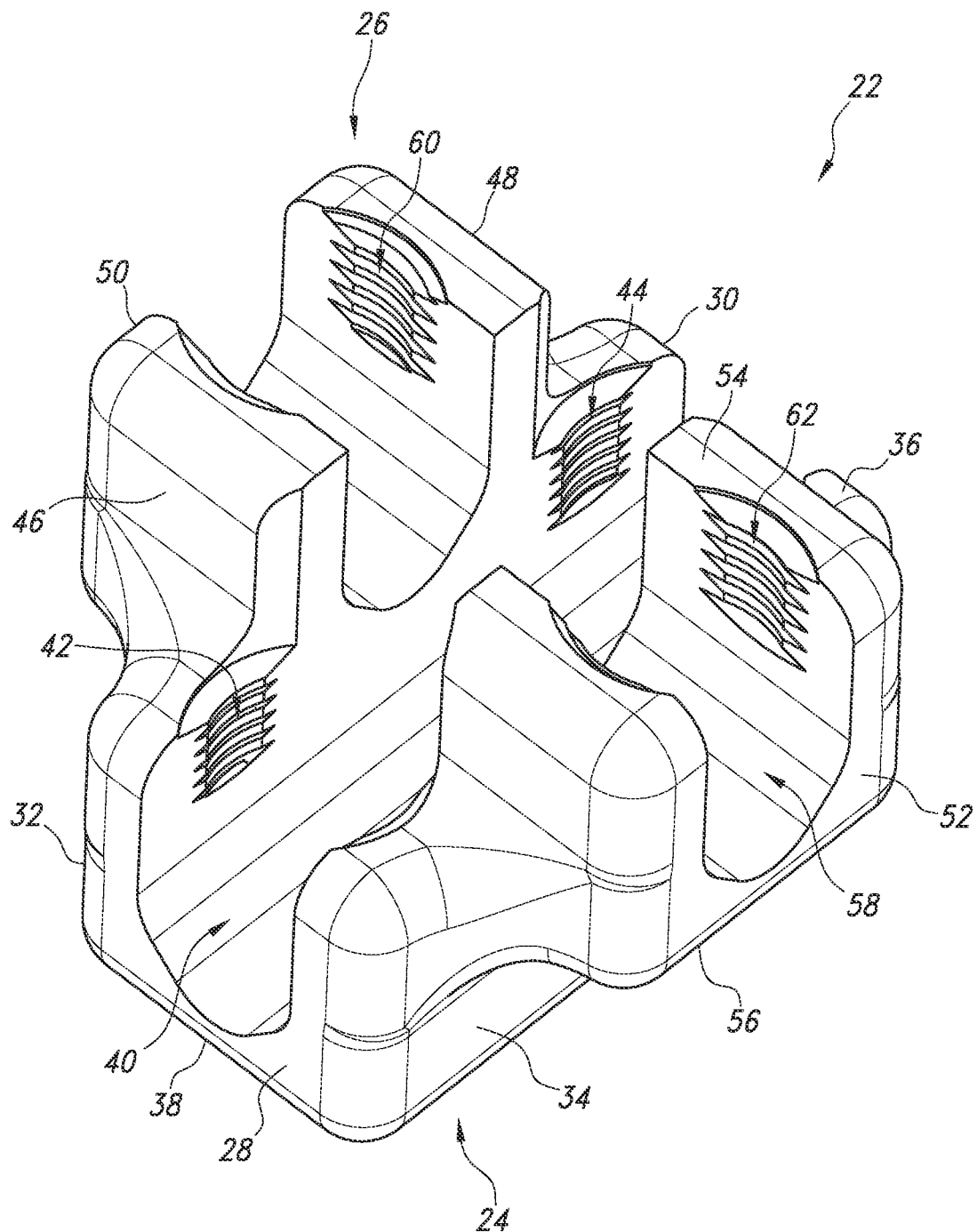
FIG. 9 is a perspective view of one embodiment of the spinal implant shown in FIG. 1, in accordance with the principles of the present disclosure.

In one embodiment, shown in FIGS. 1-7, connector 22 is configured such that surface 54 covers aperture 58 and holes 60, 62 extend through surface 54. In such embodiments, rod 64 is configured to be side loaded into aperture 40 and/or rod 66 is configured to be side loaded into aperture 58 in the direction shown by arrow A in FIG. 2 or in the direction shown by arrow B in FIG. 2. In the embodiment shown in FIGS. 1-7, surface 54 and/or surface 56 cover(s) a portion of aperture 40. In one embodiment, shown in FIG. 8, surface 54 is spaced apart from aperture 58 and/or aperture 58 extends through surface 54 such that surfaces 46, 48 define holes 60, 62. This allows rod 66 to be top loaded into aperture 58 in the direction shown by arrow C in FIG. 8 before, during, or after rod 64 is side loaded into aperture 40. In one embodiment, shown in FIG. 9, connector 22 is similar to the embodiment shown in FIG. 8 in that surface 54 is spaced apart from aperture 58 and/or aperture 58 extends through surface 54 such that surfaces 46, 48 define holes 60, 62. However, in the embodiment shown in FIG. 9, a portion of surface 56 directly above aperture 40 is removed and/or aperture 40 extends through surface 56. This allows rod 64 to be top loaded into aperture 40 in the direction shown by arrow C in FIG. 8 and then for rod 66 to be top loaded into aperture 58 in the direction shown by arrow C in FIG. 8 after rod 64 is top loaded into aperture 40.

In assembly, operation and use, system 20, similar to the systems and methods described herein, can include a one or more bone fasteners 82 in addition to connector 22, rod, 64, rod 66 and setscrews 72 and is employed with a surgical procedure for treatment of a spinal disorder affecting a section of a spine of a patient, as discussed herein. Surgical system 20 is employed with a surgical procedure for treatment of a condition or injury of an affected section of the spine. In some embodiments, one or more of bone fasteners 82 are the same or similar to one or more of the bone fasteners recited in U.S. patent application Ser. No. 16/487,057, filed on Aug. 18, 2019, U.S. patent application Ser. No. 17/744,950, filed on May 16, 2022 and/or U.S. patent application Ser. No. 17/749,920, filed on May 16, 2022. These applications are hereby incorporated herein by reference, in their entireties.

Bone fasteners 82 and one or a plurality of spinal implants, for example, spinal rods 64, 66 can be delivered or implanted as a pre-assembled device or can be assembled in situ. The components of system 20 may be completely or partially revised, removed or replaced.

Figure 7:
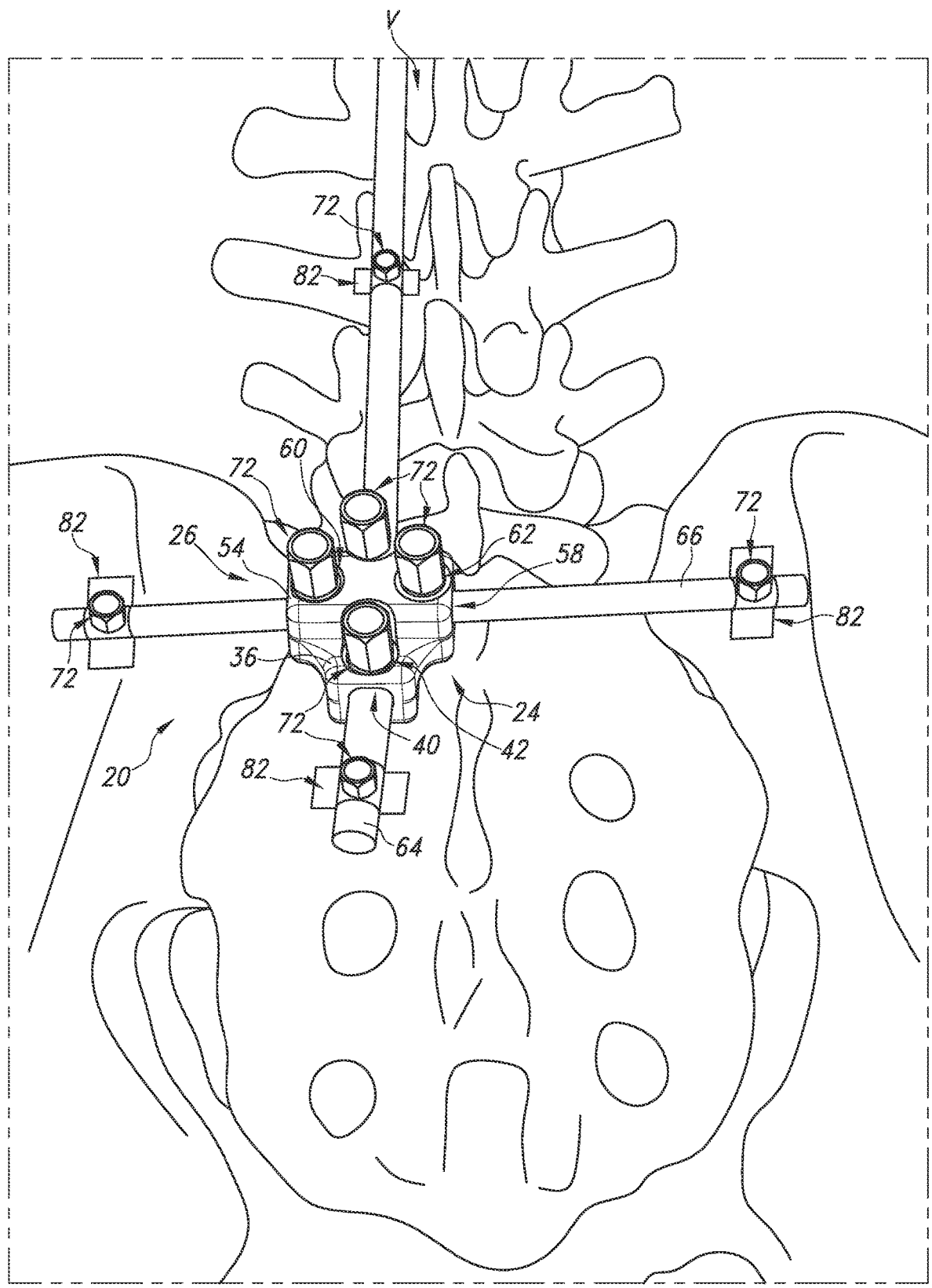
FIG. 7 is a plan view showing the rods shown in FIG. 1 disposed with the spinal implant shown in FIG. 1 and the setscrew shown in FIG. 1 disposed with the spinal implant and one of the rods.

In use, to treat a selected section of vertebrae V, as shown in FIGS. 1 and 7, a medical practitioner obtains access to a surgical site including vertebrae V in any appropriate manner, such as through incision and retraction of tissues. In some embodiments, system 20 can be used in any existing surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of system 20. A preparation instrument (not shown) can be employed to prepare tissue surfaces of vertebrae V, as well as for aspiration and irrigation of a surgical region.

One or more bone fasteners 82 is/are fixed with tissue to engage with vertebrae V along one side of vertebrae V. One or more bone fasteners 82 is/are fixed with tissue on either side of sacrum S. Connector 22 is positioned adjacent to sacrum S. Spinal rod 64 is inserted through receivers of two of bone fasteners 82 and aperture 40 of connector 22, as shown in FIG. 1. Spinal rod 66 is inserted through receivers of two of bone fasteners 82 and aperture 58 of connector 22, as also shown in FIG. 1. In some embodiments, rod 64 extends through an entire length of aperture 40 such that rod 64 extends through surfaces 28, 30 and/or rod 66 extends through an entire length of aperture 58 such that rod 66 extends through surfaces 50, 52 while rod 64 extends through an entire length of aperture 40 such that rod 64 extends through surfaces 28, 30. In some embodiments, rod 66 directly engages rod 64 when rod 66 is disposed in aperture 58 and rod 64 is disposed in aperture 40, due to the overlap/intersection of apertures 40, 58 shown in FIG. 5. In some embodiments, rod 64 and/or rod 66 is/are sized, shaped and dimensioned such that rod 66 is spaced apart from (does not directly engage) rod 64 when rod 66 is disposed in aperture 58 and rod 64 is disposed in aperture 40. Setscrews 82 engage with a surgical instrument, such as, for example, a driver (not shown), which advances setscrews 82 into engagement with the receivers of fasteners 82 to attach spinal rods 64, 66 with vertebrae V, sacrum S, etc. Setscrews 82 are threaded into engagement with holes 42, 44, as shown in FIG. 7, such that setscrews 82 directly engage rod 64 to fix rod 64 relative to connector 22. Setscrews 82 are threaded into engagement with holes 60, 62, as shown in FIG. 7, such that setscrews 82 directly engage rod 66 to fix rod 66 relative to connector 22.

In some embodiments, rods 64, 66 are fixed with vertebrae V and/or sacrum S to stabilize vertebrae V and affect growth for a correction treatment to treat spine pathologies, as described herein. In some embodiments, one or more of bone fasteners 82 are fixed with tissue, which may include selected vertebrae, for example, cervical, thoracic, lumber, sacral and/or iliac bone, one or more portions of vertebrae, for example, lamina, pedicle, spinous process, transverse process, cancellous and/or cortical bone surfaces, and/or ribs. In some embodiments, one or all of the components of system 20 can be delivered or implanted as a pre-assembled device or can be assembled in situ, in a selected order of assembly or the order of assembly of the particular components of system 20 can be varied according to practitioner preference, patient anatomy or surgical procedure parameters.

Upon completion of the procedure, the surgical instruments, assemblies and non-implanted components of system 20 are removed from the surgical site and the incision is closed. One or more of the components of system 20 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of system 20.

In some embodiments, 20 includes an agent, which may be disposed, packed, coated or layered within, on or about the components and/or surfaces of system 20. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spine rod connector, comprising:
   a first portion comprising opposite first and second end surfaces and opposite first and second side surfaces each extending from the first end surface to the second end surface, the first portion comprising opposite top and bottom surfaces, the end and side surfaces each extending from the top surface to the bottom surface, the first portion comprising a first aperture extending between and through the end surfaces and spaced apart holes extending through the top surface such that the holes are in communication with the first aperture; and
   a second portion comprising opposite first and second end surfaces and opposite first and second side surfaces each extending from the first end surface of the second portion to the second end surface of the second portion, the second portion comprising opposite top and bottom surfaces, the end and side surfaces of the second portion each extending from the top surface of the second portion to the bottom surface of the second portion, the second portion comprising a second aperture extending between and through the side surfaces of the second portion and spaced apart holes extending through the top surface of the second portion such that the holes of the second portion are in communication with the second aperture,
   wherein the first aperture is in communication with the second aperture.

2. The spine rod connector recited in claim 1, wherein the first aperture defines a first longitudinal axis disposed in a first plane and the second aperture defines a second longitudinal axis disposed in a second plane that is proximal to the first plane.

3. The spine rod connector recited in claim 1, wherein the top surface of the second portion is planar from the first end surface of the second portion to the second end surface of the second portion.

4. The spine rod connector recited in claim 1, wherein the top surface of the second portion is positioned between the top surface of the first portion and the bottom surface of the first portion.

5. The spine rod connector recited in claim 1, wherein the bottom surface of the second portion is positioned between the top surface of the first portion and the bottom surface of the first portion.

6. The spine rod connector recited in claim 1, wherein the second portion comprises a cutout extending through the first end surface of the second portion and the top surface of the second portion, the cutout being aligned with one of the holes of the first portion.

7. The spine rod connector recited in claim 1, wherein the second portion comprises a cutout extending through the second end surface of the second portion and the top surface of the second portion, the cutout being aligned with one of the holes of the first portion.

8. The spine rod connector recited in claim 1, wherein:
   the second portion comprises a first cutout extending through the first end surface of the second portion and the top surface of the second portion, the first cutout being aligned with one of the holes of the first portion; and
   the second portion comprises a second cutout extending through the second end surface of the second portion and the top surface of the second portion, the second cutout being aligned with another one of the holes of the first portion.

9. The spine rod connector recited in claim 1, wherein the first portion includes only the first aperture extending through the end surfaces of the first portion and the second portion includes only the second aperture extending through the side surfaces of the second portion.

10. The spine rod connector recited in claim 1, wherein the holes of the second portion are positioned between the holes of the first portion.

11. The spine rod connector recited in claim 1, wherein the first aperture extends perpendicular to the second aperture.

12. The spine rod connector recited in claim 1, wherein the holes are each threaded for engagement with a threaded setscrew.

13. The spine rod connector recited in claim 1, wherein the second portion is monolithically formed with the first portion.

14. The spine rod connector recited in claim 1, wherein the first aperture is positioned between the holes of the second portion.

15. A surgical system comprising:
   the spine rod connector recited in claim 1;
   a first spinal rod positioned in the first aperture; and
   a second spinal rod positioned in the second aperture.

16. The surgical system recited in claim 15, wherein the first aperture and the first spinal rod each have a non-circular diameter, are textured or are both textured and have a non-circular diameter to prevent rotation of the first spinal rod within the first aperture and the second aperture and the second spinal rod each have a non-circular diameter, are textured or are both textured and have a non-circular diameter to prevent rotation of the second spinal rod within the second aperture.

17. The surgical system recited in claim 15, further comprising:
   setscrews disposed in the holes of the first portion to fix the first spinal rod relative to the spine rod connector; and
   setscrews disposed in the holes of the second portion to fix the second spinal rod relative to the spine rod connector.

18. A spine rod connector, comprising:
   a first portion comprising opposite first and second end surfaces and opposite first and second side surfaces each extending from the first end surface to the second end surface, the first portion comprising opposite top and bottom surfaces, the end and side surfaces each extending from the top surface to the bottom surface, the first portion comprising a first aperture extending between and through the end surfaces and spaced apart holes extending through the top surface such that the holes are in communication with the first aperture; and
   a second portion comprising opposite first and second end surfaces and opposite first and second side surfaces each extending from the first end surface of the second portion to the second end surface of the second portion, the second portion comprising opposite top and bottom surfaces, the end and side surfaces of the second portion each extending from the top surface of the second portion to the bottom surface of the second portion, the second portion comprising a second aperture extending between and through the side surfaces of the second portion and spaced apart holes extending through the top surface of the second portion such that the holes of the second portion are in communication with the second aperture,
   wherein the second portion comprises a cutout extending through the first end surface of the second portion and the top surface of the second portion, the cutout being aligned with one of the holes of the first portion.

19. The spine rod connector recited in claim 18, wherein the first aperture defines a first longitudinal axis disposed in a first plane and the second aperture defines a second longitudinal axis disposed in a second plane that is proximal to the first plane.

20. A spine rod connector, comprising:
   a first portion comprising opposite first and second end surfaces and opposite first and second side surfaces each extending from the first end surface to the second end surface, the first portion comprising opposite top and bottom surfaces, the end and side surfaces each extending from the top surface to the bottom surface, the first portion comprising a first aperture extending between and through the end surfaces and spaced apart holes extending through the top surface such that the holes are in communication with the first aperture; and
   a second portion comprising opposite first and second end surfaces and opposite first and second side surfaces each extending from the first end surface of the second portion to the second end surface of the second portion, the second portion comprising opposite top and bottom surfaces, the end and side surfaces of the second portion each extending from the top surface of the second portion to the bottom surface of the second portion, the second portion comprising a second aperture extending between and through the side surfaces of the second portion and spaced apart holes extending through the top surface of the second portion such that the holes of the second portion are in communication with the second aperture,
   wherein the holes of the second portion are positioned between the holes of the first portion.

* * * * *